US012115260B2

(12) United States Patent
Gottstein et al.

(10) Patent No.: US 12,115,260 B2
(45) Date of Patent: Oct. 15, 2024

(54) TABLETS WITH HIGH ACTIVE INGREDIENT CONTENT OF OMEGA-3 FATTY ACID AMINO ACID SALTS

(71) Applicant: Evonik Operations GmbH, Essen (DE)

(72) Inventors: Thomas Gottstein, Babenhausen (DE); Guenter Knaup, Bruchkoebel (DE); Michael Schwarm, Alzenau (DE)

(73) Assignee: Evonik Operations GmbH, Essen (DE)

( * ) Notice: Subject to any disclaimer, the term of this patent is extended or adjusted under 35 U.S.C. 154(b) by 193 days.

(21) Appl. No.: 16/304,178

(22) PCT Filed: May 24, 2017

(86) PCT No.: PCT/EP2017/062592
§ 371 (c)(1),
(2) Date: Nov. 23, 2018

(87) PCT Pub. No.: WO2017/202942
PCT Pub. Date: Nov. 30, 2017

(65) Prior Publication Data
US 2020/0315970 A1 Oct. 8, 2020

(30) Foreign Application Priority Data
May 25, 2016 (EP) .................. 16171296

(51) Int. Cl.
*A61K 9/20* (2006.01)
*A23L 33/115* (2016.01)
(Continued)

(52) U.S. Cl.
CPC .......... *A61K 9/2027* (2013.01); *A23L 33/115* (2016.08); *A23L 33/17* (2016.08);
(Continued)

(58) Field of Classification Search
CPC .............. A61K 2300/00; A61K 31/202; A61K 31/198; A61K 45/06; A61K 9/2013; A61K 9/2027; A61K 9/2095; A61K 9/2009; A61K 9/2018; A61K 9/2054; A61K 9/2059; A61K 47/183; A61K 47/22; A61K 9/0014; A61K 9/0048; A61K 9/0053; A61K 9/1075; A61K 9/127; A61K 9/282; A61K 9/2886; A61K 47/542; A61K 47/55; A61K 31/4406; A61K 31/455; A61K 31/44; A61K 41/0038; A61K 31/20; A61K 9/107; A61K 31/195; A61K 9/2846; A61K 9/4891; A61K 31/557; A61K 9/28; A61K 31/385; A61K 31/225; A61K 47/50; A61K 31/197; A61K 31/221; A61K 31/4015; A61K 31/495; A61K 31/593; A61K 31/095; A61K 31/105; A61K 31/121; A61K 31/355; A61K 47/54; A61K 31/519; A61K 31/59; A61K 31/675; A61K 31/714; A61K 31/40; A61K 31/4415; A61K 31/4458; A61K 31/592; A61K 33/26; A61K 33/30; A61K 36/53; A61K 31/232; A61K 31/60; A61K 31/404; A61K 31/4468; A61K 31/575; A61K 31/609; A61K 31/12; A61K 31/165; A61K 31/216; A61K 31/22; A61K 31/341; A61K 31/352; A61K 31/366; A61K 31/375; A61K 31/401; A61K 31/4025; A61K 31/403; A61K 31/4178; A61K 31/4184; A61K 31/4418; A61K 31/4439; A61K 31/444; A61K 31/4545; A61K 31/496; A61K 31/4965; A61K 31/497; A61K 31/505; A61K 31/506; A61K 31/5377; A61K 31/713; A61K 36/61; A61K 9/0056; A61K 31/00; A61K 31/122; A61K 31/16; A61K 31/19; A61K 31/192; A61K 31/397; A61K 31/4402; A61K 31/51; A61K 31/525; A61K 31/70; A61K 31/7135; A61K 33/10; A61K 35/60; A61K 35/618; A61K 36/02; A61K 36/71; A61K 38/185; A61K 47/10; A61K 47/14; A61K 47/20; A61K 47/26; A61K 47/36; A61K 47/42; A61K 47/543; A61K 9/16; A61K 9/1617; A61K 9/1652; A61K 9/205; A61K 9/2063;
(Continued)

(56) References Cited

U.S. PATENT DOCUMENTS

| 5,750,572 | A | 5/1998 | Bruzzese |
| 5,776,978 | A | 7/1998 | Bruzzese |
| 2010/0215758 | A1* | 8/2010 | Opheim ............... A23L 33/30 424/493 |

FOREIGN PATENT DOCUMENTS

| DE | 39 07 649 A1 | 9/1989 |
| EP | 0 699 437 A1 | 3/1996 |

(Continued)

OTHER PUBLICATIONS

International Search Report and Written Opinion issued Jul. 19, 2017 in PCT/EP2017/062592 filed May 24, 2017.
(Continued)

*Primary Examiner* — Audrea B Coniglio
(74) *Attorney, Agent, or Firm* — Oblon, McClelland, Maier & Neustadt, L.L.P.

(57) ABSTRACT

The present invention relates to a tablet comprising one or more omega-3 fatty acid amino acid salt(s), a method for preparing a tablet according to the invention and the use of a tablet according to the invention as a food supplement or as a pharmaceutical product.

23 Claims, No Drawings

(51) Int. Cl.
  *A23L 33/17*     (2016.01)
  *A61K 31/198*    (2006.01)
  *A61K 31/202*    (2006.01)

(52) U.S. Cl.
  CPC .......... *A61K 9/2009* (2013.01); *A61K 9/2018* (2013.01); *A61K 9/2054* (2013.01); *A61K 9/2059* (2013.01); *A61K 9/2095* (2013.01); *A61K 31/198* (2013.01); *A61K 31/202* (2013.01)

(58) Field of Classification Search
  CPC ...... A61K 9/2833; A61K 9/284; A61K 9/286; A61K 9/2866; A61K 9/48; A61K 9/4808; A61K 9/5021; A23L 33/115; A23L 33/12; A23L 33/175; A23L 33/17; A23L 33/135; A23V 2200/30; A23V 2250/1868; A23V 2250/187; A23V 2200/304; A23V 2200/308; A23V 2200/318; A23V 2200/32; A23V 2200/324; A23V 2200/326; A23V 2200/328; A23V 2250/00; A23V 2250/1862; A23V 2250/1872; A23V 2250/1882; A23V 2002/00; A61P 3/10; A61P 3/00; A61P 3/06; A61P 9/10; A61P 25/00; A61P 27/02; A61P 9/00; A61P 43/00; A61P 3/08; A61P 13/12; A61P 1/16; A61P 37/00; A61P 25/28; A61P 7/00; A61P 3/04; A61P 29/00; A61P 25/16; A61P 9/04; A61P 5/48; A61P 17/06; A61P 25/14; A61P 17/00; A61P 37/02; A61P 5/00; A61P 5/50; A61P 35/00; A61P 9/06; A61P 21/02; A61P 7/10; A61P 11/06; A61P 1/00; A61P 21/00; A61P 31/00; A61P 19/02; A61P 11/00; A61P 25/08; A61P 25/02; A61P 27/16; A61P 37/06; A61P 17/10; A61P 3/02; A61P 1/04; A61P 27/00; A61P 27/04; A61P 19/10; A61P 31/12; A61P 39/06; A61P 1/14; A61P 1/18; A61P 15/00; A61P 15/10; A61P 15/12; A61P 17/02; A61P 17/04; A61P 17/14; A61P 17/16; A61P 19/06; A61P 25/04; A61P 25/06; A61P 25/18; A61P 25/20; A61P 25/22; A61P 25/24; A61P 29/02; A61P 31/04; A61P 37/08; A61P 41/00; A61P 5/24; A61P 7/06; A61P 9/12
  See application file for complete search history.

(56) References Cited

FOREIGN PATENT DOCUMENTS

| | | | |
|---|---|---|---|
| EP | 0 734 373 A1 | 10/1996 | |
| WO | WO 95/16661 A1 | 6/1995 | |
| WO | WO2008146016 A2 * | 12/2008 | ............. A61K 47/48 |

OTHER PUBLICATIONS

U.S. Appl. No. 16/304,227, filed Nov. 23, 2018, Guenter Knaup, et al.
U.S. Appl. No. 16/304,178, filed Nov. 23, 2018, Thomas Gottstein, et al.

* cited by examiner

TABLETS WITH HIGH ACTIVE INGREDIENT CONTENT OF OMEGA-3 FATTY ACID AMINO ACID SALTS

CROSS-REFERENCE TO RELATED APPLICATIONS

The present application is the national stage of international application PCT/EP2017/062592, filed on May 24, 2017, and claims the benefit of the filing date of European Appl. No. 16171296.3, filed on May 25, 2016.

Omega-3 fatty acids, particularly eicosapentaenoic acid (EPA) and docosahexaenoic acid (DHA), are linked to numerous positive health effects on the cardiovascular system, on inflammatory disorders, on brain development and function, on disruptions of the central nervous system and on other areas (C. H. S. Ruxton, S. C. Reed, M. J. A. Simpson, K. J. Millington, J. Hum. Nutr. Dietet 2004, 17, 449). Therefore, the intake of omega-3 fatty acids is supported by statements of regulatory agencies. For instance, the EFSA (European Food Safety Authority) recommends for adults a daily intake of 250 mg of EPA+DHA (EFSA Panel on Dietetic Products, Nutrition and Allergies, EFSA Journal 2010, 8 (3), 1461). The AHA (American Heart Association) advises the intake of at least two meals of fatty fish per week for persons without documented cardiovascular disorders, the intake of about 1 g of EPA+DHA per day from fish or food supplements for persons with documented cardiovascular disorders and the intake of 2-4 g of EPA+DHA per day for the treatment of raised blood lipid values (P. M. Kris-Etherton, W. S. Harris, L. J. Appel, Circulation 2002, 106, 2747). Moreover, the authorities have expressly approved health claims for omega-3 fatty acids determined on the basis of clinical studies (EU Register on Nutrition and Health Claims; see also: EFSA Journal 2011, 9 (4), 2078). Therefore, omega-3 fatty acids, especially from fish oil but also from other plant or microbial sources, are increasingly used as food supplements, food additives and medicaments.

According to standard nomenclature, polyunsaturated fatty acids are classified according to the number and position of the double bonds. There are two series or families, depending on the position of the double bond which is closest to the methyl end of the fatty acid. The omega-3 series comprises a double bond at the third carbon atom whereas the omega-6 series has no double bond up to the sixth carbon atom. Thus, docosahexaenoic acid (DHA) has a chain length of 22 carbon atoms with 6 double bonds beginning with the third carbon atom from the methyl end and is referred to as "22:6 n-3" (all-cis-4,7,10,13,16,19-docosahexaenoic acid). Another important omega-3 fatty acid is eicosapentaenoic acid (EPA), which is referred to as "20:5 n-3" (all-cis-5,8,11,14,17-eicosapentaenoic acid).

Most of the omega-3 fatty acid products introduced to the market are offered in the form of oils, starting from fish oil with a content of about 30% omega-3 fatty acids up to concentrates with over 90% content of EPA or DHA or mixtures of these two omega-3 fatty acids. The formulations used are predominantly soft gelatine capsules. In addition, numerous further product forms have been described, such as microencapsulations or powder preparations (C. J. Barrow, B. Wang, B. Adhikari, H. Liu, Spray drying and encapsulation of omega-3 oils, in: Food enrichment with omega-3 fatty acids (Eds.: C. Jacobsen, N. S. Nielsen, A. Frisenfeldt Horn, A.-D. Moltke Soerensen), pp. 194-225, Woodhead Publishing Ltd., Cambridge 2013, ISBN 978-0-85709-428-5; T.-L. Torgersen, J. Klaveness, A. H. Myrset, US 2012/0156296 A1). Chemically, these are usually triglycerides or fatty acid ethyl esters with various concentrations of omega-3 fatty acids, while phospholipids, e.g. as krill oil, free fatty acids (T. J. Maines, B. N. M. Machielse, B. M. Mehta, G. L. Wisler, M. H. Davidson, P. R. Wood, US 2013/0209556 A1; M. H. Davidson, G. H. Wisler, US 2013/0095179 A1; N. J. Duragkar, US 2014/0018558 A1; N. J. Duragkar, US 2014/0051877 A1) and various salts of fatty acids are also known, e.g. with potassium, sodium, ammonium (H. J. Hsu, S. Trusovs, T. Popova, U.S. Pat. No. 8,203,013 B2), calcium and magnesium, (J. A. Kralovec, H. S. Ewart, J. H. D. Wright, L. V. Watson, D. Dennis, C. J. Barrow, J. Functional Foods 2009, 1, 217; G. K. Strohmaier, N. D. Luchini, M. A. Varcho, E. D. Frederiksen, U.S. Pat. No. 7,098,352 B2), where these salts are not water-soluble, aminoalcohols (P. Rongved, J. Klaveness, US 2007/0213298 A1), amine compounds such as piperazine (B. L. Mylari, F. C. Sciavolino, US 2014/0011814 A1), and guanidine compounds such as metformin (M. Manku, J. Rowe, US 2012/0093922 A1; B. L. Mylari, F. C. Sciavolino, US 2012/0178813 A1; B. L. Mylari, F. C. Sciavolino, US 2013/0281535 A1; B. L. Mylari, F. C. Sciavolino, WO 2014/011895 A2). The bioavailability of the different omega-3 derivatives for the human body is very diverse. Since omega-3 fatty acids as free fatty acids together with monoacyl glycerides are absorbed in the small intestine, the bioavailability of free omega-3 fatty acids is better than that of triglycerides or ethyl esters since these have firstly to be cleaved to the free fatty acids in the digestive tract (J. P. Schuchhardt, A. Hahn, Prostaglandins Leukotrienes Essent. Fatty Acids 2013, 89, 1). The stability to oxidation is also very different in different omega-3 derivatives. Free omega-3 fatty acids are described as very sensitive to oxidation (J. P. Schuchhardt, A. Hahn, Prostaglandins Leukotrienes Essent. Fatty Acids 2013, 89, 1). For the use of a solid omega-3 form, an increased stability compared to liquid products is assumed (J. A. Kralovec, H. S. Ewart, J. H. D. Wright, L. V. Watson, D. Dennis, C. J. Barrow, J. Functional Foods 2009, 1, 217).

Furthermore, preparations of omega-3 fatty acids with diverse amino acids, such as lysine and arginine, are known, either as mixtures (P. Literati Nagy, M. Boros, J. Szilbereky, I. Racz, G. Soos, M. Koller, A. Pinter, G. Nemeth, D E 3907649 A1) or as salts (B. L. Mylari, F. C. Sciavolino, WO 2014/011895 A1; T. Bruzzese, EP 0699437 A1; T. Bruzzese, EP0734373 B1; T. Bruzzese, U.S. Pat. No. 5,750,572; J. Torras et al., Nephron 1994, 67, 66; J. Torras et al., Nephron 1995, 69, 318; J. Torras et al., Transplantation Proc. 1992, 24 (6), 2583; S. El Boustani et al., Lipids 1987, 22 (10), 711; H. Shibuya, US 2003/0100610 A1). The preparation of omega-3 aminoalcohol salts by spray-drying is also mentioned (P. Rongved, J. Klaveness, US 2007/0213298 A1). In general form, the preparation of DHA amino acid salts is described by evaporation to dryness under high vacuum and low temperature or freeze-drying (T. Bruzzese, EP0734373 B1 and U.S. Pat. No. 5,750,572). The resulting products are described as very thick, transparent oils which transform at low temperature into solids of waxy appearance and consistency.

Finally, processing of omega-3 amino acid preparations to tablets is known in principle. The concentrations of omega-3 fatty acids in the finished tablets, owing to the presence of amino acids in the preparations and the additional use of auxiliaries such as binders, release agents and structure-forming substances, is at most 38% in the case of omega-3 amino acid salts (T. Bruzzese, EP0734373 B1 and U.S. Pat. No. 5,750,572, Example 15), or at most 34.6% in the case of omega-3 fatty acid amino acid mixtures (P. Literati Nagy, M.

Boros, J. Szilbereky, I. Racz, G. Soos, M. Koller, A. Pinter, G. Nemeth, D E 3907649 A1), according to the formulae mentioned in the examples.

However, despite the extensive prior art, all the known product forms have one or more disadvantages such that further improvement needs exist. For instance, the most common omega-3 triglyceride and ethyl ester oils are inherently less readily bioavailable than the free omega-3 fatty acids. These are in turn particularly sensitive to oxidation. The established formulation as a soft gelatine capsule is more complicated, more expensive and more prone to defects than a simple tabletting of a solid. In addition, many consumers oppose the consumption of gelatine of animal origin on religious or other grounds. Solid omega-3 formulations described to date, either as microencapsulated or bound oil, as mixtures with amino acids or as salts, have other serious disadvantages. For instance, alkali metal salts are strongly alkaline in aqueous solution whereas alkaline earth metal salts are practically water-insoluble which limits the bioavailability. Although mixtures or salts with amino acids are soluble and should therefore be readily bioavailable, the tablets described still have relatively low omega-3 fatty acid contents of at most 38% for salts of omega-3 fatty acids and amino acids and at most 34.6% for mixtures of omega-3 fatty acids and amino acids. This relies on large amounts of added auxiliaries such as release agents and binders and structure-forming substances which are used for the preparation of a stable tablet. The low omega-3 fatty acid contents lead however to the fact that the consumer must take the corresponding products frequently and in relatively large amounts in order to reach the recommended daily intake amounts, which may be several 100 milligrams up to a few grams per day depending on the country and health condition.

Due to the disadvantages described, a need exists for solid omega-3 fatty acid preparations which can be readily and cost-effectively formulated as tablets, which have better bioavailability and in addition are also more stable than standard liquid formulations, and which in addition are as highly concentrated in omega-3 fatty acids as possible in order to keep the daily intake amount as low as possible.

It has now been found, surprisingly, that tablets comprising one or more omega-3 fatty acid amino acid salt(s) are obtainable, in which the content of binders and structure-forming substances selected from the group consisting of polyvinylpyrrolidone (PVP), starch, lactose, microcrystalline cellulose, calcium sulphate, mannitol, calcium phosphate and mixtures thereof is in total 40% by weight or less, based on the total weight of the tablet.

The present invention accordingly relates in a first aspect to a tablet comprising one or more omega-3 fatty acid amino acid salt(s), characterized in that the content of binders and structure-forming substances selected from the group consisting of polyvinylpyrrolidone (PVP), starch, lactose, microcrystalline cellulose, calcium sulphate, mannitol, calcium phosphate and mixtures thereof is in total 40% by weight or less, based on the total weight of the tablet.

In a preferred configuration of the present invention, the content of binders and structure-forming substances selected from the group consisting of polyvinylpyrrolidone (PVP), starch, lactose, microcrystalline cellulose, calcium sulphate, mannitol, calcium phosphate and mixtures thereof is in total 20% by weight or less, more preferably 10% by weight or less, particularly preferably 1% by weight or less, based on the total weight of the tablet. In a further preferred configuration of the present invention, a tablet according to the invention is free of binders and structure-forming substances selected from the group consisting of polyvinylpyrrolidone (PVP), starch, lactose, microcrystalline cellulose, calcium sulphate, mannitol, calcium phosphate and mixtures thereof.

Particularly surprising was the finding that omega-3 fatty acid amino acid salt(s) with addition of only few auxiliaries, in particular in particularly advantageous cases without the addition of either binders or structure—forming substances, can be compressed to give tablets. Finally, the preparation of tablets by direct compression has generally been described only for a few substances such as calcium sulphate, calcium hydrogen phosphate, (microcrystalline) cellulose, lactose or other sugar and sugar derivatives, but not for omega-3 fatty acids or derivatives thereof (Pharmazeutische Hilfsstoffe [Pharmaceutical Auxiliaries], Peter C. Schmidt, Siegfried Lang, p. 131f., GOVI-Verlag, ISBN 978-3-7741-1222-3).

Omega-3 fatty acids, which may be present individually or in any preferred combination in a tablet according to the invention, comprise for example eicosatrienoic acid (ETE) 20:3 (n-3) (all-cis-11,14,17-eicosatrienoic acid), eicosatetraenoic acid (ETA) 20:4 (n-3) (all-cis-8,11,14,17-eicosatetraenoic acid), heneicosapentaenoic acid (HPA) 21:5 (n-3) (all-cis-6,9,12,15,18-heneicosapentaenoic acid), docosapentaenoic acid (clupanodonic acid) (DPA) 22:5 (n-3) (all-cis-7,10,13,16,19-docosapentaenoic acid, tetracosapentaenoic acid 24:5 (n-3) (all-cis-9,12,15,18,21-tetracosapentaenoic acid), tetracosahexaenoic acid (nisinic acid) 24:6 (n-3) (all-cis-6,9,12,15,18,21-tetracosahexaenoic acid).

Omega-3 fatty acids may be obtained from any suitable starting material, which may in addition be processed with any suitable method. Typical starting materials include all parts of fish carcasses, vegetables and other plants, and also material from microbial fermentation or fermentation of algae. Typical processing methods for such starting materials are, inter alia, steps for crude oil extraction, such as extraction and separation of the starting materials and also steps for refining crude oils, such as deposition and degumming, deacidification, bleaching and deodourizing (cf. e.g. "EFSA Scientific Opinion on Fish Oil for Human Consumption"). Further processing methods include, inter alia, steps for the at least partial conversion of omega-3 fatty acid esters to the corresponding free omega-3 fatty acids or inorganic salts thereof.

Omega-3 fatty acids may also be obtained by cleaving the omega-3 fatty acid esters and subsequent removal of the alcohols previously attached as part of the ester from compositions which consist principally of omega-3 fatty acid esters. The ester cleavage is preferably carried out under basic conditions. Methods for ester cleavage are well known from the prior art.

The stability of a tablet according to the invention is not dependent on whether the fatty acid component is, for example, a hydrolysate of an EPA or DHA concentrate, of an EPA/DHA semi-concentrate or even a fish oil.

In an advantageous configuration of the present invention, the omega-3 fatty acid(s) is/are selected from eicosapentaenoic acid (EPA), docosahexaenoic acid (DHA) and mixtures of the same.

In a further advantageous configuration of the present invention, the amino acid(s) is/are selected from basic amino acids, preferably from lysine, arginine, ornithine and mixtures of the same.

When using omega-3 fatty acid amino acid salts which have been prepared from sufficiently highly concentrated EPA or DHA starting materials or EPA/DHA mixtures, the resulting tablets may have a content of omega-3 fatty acids of over 40% in total. In the case of such high omega-3 fatty acid contents, the intake of only a few tablets is sufficient, possibly only one single tablet per day, in order to reach the recommended daily intake amount of omega-3 fatty acids.

Therefore, in an advantageous configuration of the present invention, the content of omega-3 fatty acids is in total 40% by weight or more, particularly preferably 50% by weight or more, based on the total weight of the tablet.

The salts of omega-3 fatty acids and amino acids are dissolved in the digestive tract, wherein the free omega-3 fatty acids are released which are suitable for direct absorption by the body, and prior chemical or enzymatic cleavage is no longer required, such as is the case in the omega-3 triglycerides in fish oil or the omega-3 fatty acid ethyl esters prepared therefrom.

In a further aspect, the present invention relates to a method for preparing a tablet according to the invention, characterized in that the omega-3 fatty acid amino acid salt(s) is/are compressed, optionally together with one or more binder(s) and/or one or more structure—forming substance(s).

In a preferred configuration, the method according to the invention is characterized in that the omega-3 fatty acid amino acid salt(s) is/are compacted prior to the compression. The compaction can be accomplished, for example, using an Exzenter tablet press with 25 mm biplanar punches at a compression force of 15-20 kN (30.5-40.7 MPa). The resulting product can subsequently be crumbled again via a 1 mm sieve.

In a further preferred configuration, the method according to the invention is characterized in that the omega-3 fatty acid amino acid salt(s) is/are granulated preferably with a solvent, water or ethanol for example, or with a solvent mixture, a water/ethanol mixture for example, prior to the compression and optionally prior to the compaction.

Omega-3 fatty acid amino acid salts are known in principle. As described at the outset, these may be obtained as fine, virtually colourless powders by precipitation from aqueous or aqueous alcoholic media or by spray-drying, which differ advantageously from the waxy consistency of these substances described hitherto.

In a preferred configuration, the method according to the invention is characterized in that the omega-3 fatty acid amino acid salt(s) is/are obtained by precipitation from aqueous or alcoholic aqueous solution.

In a further preferred configuration, the method according to the invention is characterized in that the omega-3 fatty acid amino acid salt(s) is/are obtained by spray-drying of an aqueous or alcoholic aqueous solution.

In a further aspect, the present invention relates to the use of a tablet according to the invention as a food supplement or pharmaceutical product.

In the context of the present invention, pharmaceutical products may comprise, in addition to the omega-3 fatty acids described here, both pharmaceutically acceptable auxiliaries and pharmaceutical active ingredients such as statins, anti-hypertensive agents, antidiabetics, antidementia agents, antidepressants, anti-obesity agents, appetite suppressants and agents to improve memory and/or cognitive function.

EXAMPLE 1

| Material | Amount [% by weight] | Amount [g] |
|---|---|---|
| Omega-3 fatty acid lysine salt | 85.00 | 255.00 |
| Mg stearate | 1.00 | 3.00 |
| Cornstarch (cold swelling) | 6.50 | 19.50 |
| PVP | 6.50 | 19.50 |
| Aerosil 200 Pharma (highly dispersed silicon dioxide) | 1.00 | 3.00 |
| Sum total | 100.00 | 300.00 |

The formula could be compressed with 21×9 mm oblong punches at 5 kN compression force to 50 N hard tablets. The omega-3 fatty acid lysine salt used had a content of omega-3 fatty acids (sum of EPA+DHA) of 48% by weight. This resulted in a content of omega-3 fatty acids of the finished tablets of 41% by weight.

EXAMPLE 2

| Material | Amount [% by weight] |
|---|---|
| Omega-3 fatty acid lysine salt (EPA-lysinate) | 86.40 |
| Na starch glycolate | 2.90 |
| Hydroxy-propyl-methyl-cellulose (HPMC E5) | 2.10 |
| Talkum | 4.00 |
| Aerosil 200 Pharma (highly dispersed silicon dioxide) | 3.00 |
| Mg-stearate | 1.60 |
| Sum total | 100.00 |

This formula could also directly be compressed to tablets. The omega-3 fatty acid lysine salt used had a content of omega-3 fatty acids (EPA) of 65% by weight. This resulted in a content of omega-3 fatty acids of the finished tablets of 56.1%.

The invention claimed is:

1. A tablet, comprising:
eicosapentaenoic acid combined with a first basic amino acid as an EPA salt;
docosahexaenoic acid combined with a second basic amino acid as a DHA salt;
a total amount of 20 wt. % or less, based on a total tablet weight, of a binder and/or a structure-forming substance selected from the group consisting of polyvinylpyrrolidone, starch, lactose, microcrystalline cellulose, calcium sulfate, mannitol, calcium phosphate, and a mixture thereof,
wherein the EPA and DHA salts are present as a mixture in powder form, and
wherein a sum of the eicosapentaenoic acid and the docosahexaenoic acid in the tablet is 40 wt. % or more, based on the total tablet weight and measured in free acid form.

2. The tablet of claim 1, comprising, based on the total tablet weight, a total amount of no more than 10 wt. % of the binder and/or the structure-forming substance.

3. The tablet of claim 1, wherein omega-3 fatty acids present in the tablet consist essentially of eicosapentaenoic acid and docosahexaenoic acid.

4. The tablet of claim 1, wherein the first and second basic amino acid are independently selected from the group consisting of lysine, arginine, ornithine, and a mixture thereof.

5. The tablet of claim 1, comprising the eicosapentaenoic acid and the docosahexaenoic acid in the tablet is 50 wt. % or more, based on the total tablet weight and measured in free acid form.

6. A method of preparing the tablet of claim 1, the method comprising:
compressing the EPA salt and the DHA salt, optionally together with the binder and/or the structure-forming substance.

7. The method of claim 6, comprising:
compacting the EPA salt and the DHA salt prior to the compressing.

8. The method of claim 6, comprising:
granulating the EPA salt and the DHA salt with a solvent or a solvent mixture prior to the compressing.

9. The method of claim 6, comprising:
precipitating the EPA salt and the DHA salt from an aqueous or alcoholic aqueous solution.

10. The method of claim 6, comprising:
spray-drying of an aqueous or alcoholic aqueous solution of the first and second basic amino acid, the eicosapentaenoic acid, and the docosahexaenoic acid to obtain the EPA salt and the DHA salt.

11. A food supplement or a pharmaceutical product, comprising:
the tablet of claim 1.

12. The method of claim 7, comprising:
granulating the EPA salt and the DHA salt with a solvent or a solvent mixture prior to the compacting.

13. The tablet of claim 1, comprising the binder and/or a structure-forming substance in no more than 1 wt. %.

14. The tablet of claim 1, wherein the binder and/or a structure-forming substance is selected from the group consisting of polyvinylpyrrolidone, starch, lactose, calcium sulfate, mannitol, calcium phosphate, and a mixture of two or more of any of these.

15. The tablet of claim 1, comprising no microcrystalline cellulose.

16. The tablet of claim 1, comprising the eicosapentaenoic acid and the docosahexaenoic acid in the tablet, together, in 41 wt. % or more, based on the total tablet weight and measured in free acid form.

17. The tablet of claim 1, comprising the eicosapentaenoic acid and the docosahexaenoic acid in the tablet, together, in 56.1 wt. % or more, based on the total tablet weight and measured in free acid form.

18. The tablet of claim 1, comprising only the eicosapentaenoic acid and docosahexaenoic acid as omega-3 fatty acids.

19. A tablet, comprising:
an EPA salt of a first basic amino acid and eicosapentaenoic acid;
a DHA salt of a basic amino acid and docosahexaenoic acid; and optionally
a total amount of no more 10 wt. %, based on a total tablet weight, of a binder and/or a structure-forming substance selected from the group consisting of polyvinylpyrrolidone, starch, lactose, microcrystalline cellulose, calcium sulfate, mannitol, calcium phosphate, and a mixture thereof,
wherein a sum of the eicosapentaenoic acid and the docosahexaenoic acid in the tablet is 41 wt. % or more, based on the total tablet weight and measured in free acid form,
wherein the first and second basic amino acid are selected from the group consisting of lysine, arginine, ornithine, and a mixture thereof,
wherein the EPA salt and DHA salt are present as a mixture in powder form.

20. The tablet of claim 19, wherein the sum of the eicosapentaenoic acid and the docosahexaenoic acid in the tablet is 50 wt. % or more, based on the total tablet weight and measured in free acid form.

21. The tablet of claim 19, wherein the EPA salt and the DHA salt are obtained by a process comprising:
(i) precipitating the EPA salt and the DHA salt from an aqueous or alcoholic aqueous solution; and/or,
(ii) spray-drying of an aqueous or alcoholic aqueous solution of the first and second basic amino acid, the eicosapentaenoic acid, and the docosahexaenoic acid to obtain the EPA salt and the DHA salt, and
compressing the EPA salt and the DHA salt to form the tablet.

22. A tablet, comprising:
a salt of eicosapentaenoic acid with a first basic amino acid;
a salt of docosahexaenoic acid with a second basic amino acid;
a total amount of 20 wt. % or less, based on a total tablet weight, of a binder and/or a structure-forming substance selected from the group consisting of polyvinylpyrrolidone, starch, lactose, microcrystalline cellulose, calcium sulfate, mannitol, calcium phosphate, and a mixture thereof,
wherein a sum of the eicosapentaenoic acid and the docosahexaenoic acid in the tablet is 40 wt. % or more, based on the total tablet weight as free acids, and
wherein the eicosapentaenoic acid salt and the docosahexaenoic acid salt are in non-waxy solid form.

23. The tablet of claim 22, wherein the omega-3 fatty acids are suitable to be compacted with a tablet press into the tablet without the binder and/or the structure-forming substance.

* * * * *